US009795809B2

(12) United States Patent
Fiegel et al.

(10) Patent No.: US 9,795,809 B2
(45) Date of Patent: Oct. 24, 2017

(54) USE OF MOSS TO IMPROVE DENTAL HEALTH

(71) Applicants: Vance D. Fiegel, Shakopee, MN (US); David R. Knighton, Richmond, MN (US)

(72) Inventors: Vance D. Fiegel, Shakopee, MN (US); David R. Knighton, Richmond, MN (US)

(73) Assignee: Embro Corporation, St. Louis Park, MN (US)

( * ) Notice: Subject to any disclaimer, the term of this patent is extended or adjusted under 35 U.S.C. 154(b) by 323 days.

(21) Appl. No.: 14/580,675

(22) Filed: Dec. 23, 2014

(65) Prior Publication Data

US 2015/0174058 A1 Jun. 25, 2015

Related U.S. Application Data

(60) Provisional application No. 61/920,059, filed on Dec. 23, 2013.

(51) Int. Cl.
| | | |
|---|---|---|
| *A01N 65/00* | (2009.01) | |
| *A61Q 11/00* | (2006.01) | |
| *A61K 8/97* | (2017.01) | |

(52) U.S. Cl.
CPC .............. *A61Q 11/00* (2013.01); *A61K 8/975* (2013.01)

(58) Field of Classification Search
CPC ....................................................... A61K 36/00
USPC ......................................................... 424/725
See application file for complete search history.

(56) References Cited

U.S. PATENT DOCUMENTS

| | | | |
|---|---|---|---|
| 221,909 | A | 3/1879 | Collins |
| 239,564 | A | 3/1881 | Smith |
| 413,621 | A | 8/1889 | Glaister |
| 1,914,824 | A | 6/1933 | Eberhard |
| 2,221,815 | A | 11/1940 | Rice |
| 2,605,589 | A | 8/1952 | Kuestner |
| 2,785,106 | A | 3/1957 | Mendelsohn |
| 2,876,588 | A | 3/1959 | Tietz et al. |
| 3,635,816 | A | 1/1972 | Golub |
| 3,835,042 | A | 9/1974 | Lalancette et al. |
| 3,890,910 | A | 6/1975 | Angruner |
| 3,894,355 | A | 7/1975 | Carothers |
| 3,903,267 | A | 9/1975 | Miler et al. |
| 3,914,901 | A | 10/1975 | Muldner |
| 3,961,444 | A | 6/1976 | Skaife |
| 4,002,566 | A | 1/1977 | Smith |
| 4,014,676 | A | 3/1977 | Carter et al. |
| 4,079,543 | A | 3/1978 | Stoller |
| 4,123,359 | A | 10/1978 | Smith |
| 4,146,646 | A | 3/1979 | Percival et al. |
| 4,190,981 | A | 3/1980 | Muldner |
| 4,215,692 | A | 8/1980 | Levesque |
| 4,272,527 | A | 6/1981 | Belkevich et al. |
| 4,272,962 | A | 6/1981 | Viscovich et al. |
| 4,402,941 | A | 9/1983 | Vaillancourt |
| 4,430,785 | A | 2/1984 | Sanderson |
| 4,528,774 | A | 7/1985 | Skaife |
| 4,537,590 | A | 8/1985 | Pieniak |
| 4,551,165 | A | 11/1985 | Warner |
| 4,560,372 | A | 12/1985 | Pieniak |
| 4,588,400 | A | 5/1986 | Ring et al. |
| 4,588,693 | A | 5/1986 | Strobel |
| 4,618,496 | A | 10/1986 | Brasseur |
| 4,624,790 | A | 11/1986 | Kamperman et al. |
| 4,676,196 | A | 6/1987 | Lojek et al. |
| 4,704,818 | A | 11/1987 | Cameron |
| 4,788,146 | A | 11/1988 | Ring et al. |
| 4,798,723 | A | 1/1989 | Dart et al. |
| 4,827,871 | A | 5/1989 | Morrison |
| 4,861,481 | A | 8/1989 | Allen, III |
| 4,936,910 | A | 6/1990 | Dadgar et al. |
| 4,941,282 | A | 7/1990 | Milstein |
| 4,971,702 | A | 11/1990 | Renk |

(Continued)

FOREIGN PATENT DOCUMENTS

| | | |
|---|---|---|
| CA | 2 693 695 A1 | 1/2009 |
| CN | 1316259 A | 10/2001 |

(Continued)

OTHER PUBLICATIONS

Abstract for JP 8-1188 (1996) (1 page).
Abstract for JP 11-56096 (1999) (1 page).
Abstract for JP 2001-62478 (2001) (1 page).
Abstract for JP 2001-226991 A (2001) (1 page).
Abstract for JP 2002-360060 (2002) (1 page).
Abstract for KR20030053231A (2003) (1 page).
Abstract for WO 2004/060049 A1 (2004) (1 page). Date Unknown.
Abstract for WO 2005/081641 A2 (2005) (1 page).
Asakawa, "Biologically Active Substances Obtained From Bryophytes1.2", Journ. Hattori Bot. Lab. No. 50:123-142 (Sep. 1981).
Azegami et al., Effect of Iron Limitation on "*Pseudomonas plantarii*" Growth and Tropolone and Protein Production, AEM, 54(3):844-847 (Mar. 1988).
Banerjee et al., "Antibiotic Activity of Bryophytes1", The Bryologist, 82(2):141-153 (1979).
Borel et al., "Dicranin, an Antimicrobial and 15-Lipoxygenase Inhibitor From the Moss Dicranum Scoparium", Journal of Natural Products, 56(7):1071-1077 (Jul. 1993).

(Continued)

Primary Examiner — Michael Meller
(74) Attorney, Agent, or Firm — Popovich, Wiles & O'Connell, P.A.

(57) ABSTRACT

A method of improving dental health in a mammal in which a mammal drinks at least 0.5 liters of water per day for a majority of the days of a period of at least one month, the water having been contacted with an amount of a non-decomposed moss effective to improve dental health as evidenced by a reduction in the pocket depths of the teeth of the mammal. A method of improving dental health in a mammal in which the mammal's teeth are brushed using a toothpaste or rinsed with a mouthwash for a majority of the days of a period of at least one month, the toothpaste or mouthwash containing an amount of a non-decomposed moss or non-decomposed moss extract effective to improve dental health as evidenced by a reduction in the pocket depths of the teeth. A toothpaste or mouthwash containing an effective amount of a non-decomposed moss or non-decomposed moss extract.

19 Claims, No Drawings

(56) References Cited

U.S. PATENT DOCUMENTS

| | | |
|---|---|---|
| 4,999,202 A | 3/1991 | Cronje et al. |
| 5,049,002 A | 9/1991 | Cole |
| 5,049,265 A | 9/1991 | Boyd et al. |
| 5,060,598 A | 10/1991 | Richards |
| 5,108,614 A | 4/1992 | Ross et al. |
| 5,118,504 A | 6/1992 | Clement et al. |
| 5,178,769 A | 1/1993 | Simpson et al. |
| 5,181,802 A | 1/1993 | Thengs et al. |
| 5,187,200 A | 2/1993 | Rainer |
| 5,242,582 A | 9/1993 | Marioni |
| 5,271,987 A | 12/1993 | Iskra |
| 5,290,554 A | 3/1994 | Tolpa et al. |
| 5,296,293 A | 3/1994 | Jobst |
| 5,346,514 A | 9/1994 | Molnar et al. |
| 5,360,117 A | 11/1994 | Tolpa et al. |
| 5,360,608 A | 11/1994 | Harman et al. |
| 5,373,025 A | 12/1994 | Gay |
| 5,378,460 A | 1/1995 | Zuckerman et al. |
| 5,389,257 A | 2/1995 | Todd et al. |
| 5,403,584 A | 4/1995 | Crawford et al. |
| 5,418,165 A | 5/1995 | McBeath |
| 5,454,191 A | 10/1995 | Mayeda et al. |
| 5,476,523 A | 12/1995 | Hiraoka |
| 5,476,591 A | 12/1995 | Green |
| 5,478,463 A | 12/1995 | Brownawell et al. |
| 5,527,526 A | 6/1996 | Crawford |
| 5,533,300 A | 7/1996 | Kesler |
| 5,543,300 A | 8/1996 | Inglot et al. |
| 5,549,889 A | 8/1996 | Zuckerman et al. |
| 5,580,192 A | 12/1996 | Ogawa et al. |
| 5,584,140 A | 12/1996 | Byrne |
| 5,597,489 A | 1/1997 | Schneider et al. |
| 5,602,071 A | 2/1997 | Summers et al. |
| 5,603,941 A | 2/1997 | Farina et al. |
| 5,608,989 A | 3/1997 | Behrens |
| 5,635,029 A | 6/1997 | Levesque et al. |
| 5,688,259 A | 11/1997 | Osborn, III et al. |
| 5,690,827 A | 11/1997 | Simmering et al. |
| 5,693,220 A | 12/1997 | Sceusa |
| 5,704,989 A | 1/1998 | Page |
| 5,707,527 A | 1/1998 | Knutson et al. |
| 5,718,697 A | 2/1998 | Chauvette et al. |
| 5,747,050 A | 5/1998 | Tolpa et al. |
| 5,759,225 A | 6/1998 | Tanoshima |
| 5,797,894 A | 8/1998 | Cadieux et al. |
| 5,807,484 A | 9/1998 | Couture et al. |
| 5,814,233 A | 9/1998 | Starkey et al. |
| 5,829,193 A | 11/1998 | Otake et al. |
| 5,843,415 A | 12/1998 | Klar |
| 5,853,460 A | 12/1998 | Alcordo |
| 5,853,706 A | 12/1998 | Klar |
| 5,866,016 A | 2/1999 | Jaquess et al. |
| 5,895,380 A | 4/1999 | Turi et al. |
| 5,934,011 A | 8/1999 | Ishioka et al. |
| 5,942,478 A | 8/1999 | Lopes |
| 5,945,446 A | 8/1999 | Laub |
| 5,980,748 A | 11/1999 | Auger et al. |
| 5,997,812 A | 12/1999 | Burnham et al. |
| 6,012,251 A | 1/2000 | Siegert |
| 6,027,639 A | 2/2000 | Lenhart, Jr. et al. |
| 6,030,533 A | 2/2000 | Karamanev et al. |
| 6,036,851 A | 3/2000 | Simmering et al. |
| 6,040,032 A | 3/2000 | Isräel et al. |
| 6,042,743 A | 3/2000 | Clemenson |
| 6,048,131 A | 4/2000 | Laak |
| 6,062,220 A | 5/2000 | Whitaker et al. |
| 6,062,229 A | 5/2000 | Kandratavich et al. |
| 6,074,988 A | 6/2000 | King et al. |
| 6,096,266 A | 8/2000 | Duroselle |
| 6,100,081 A | 8/2000 | Buelna |
| 6,100,382 A | 8/2000 | Wolfe et al. |
| 6,123,036 A | 9/2000 | Decker |
| 6,132,599 A | 10/2000 | Chaffee |
| 6,187,183 B1 | 2/2001 | Weaver et al. |
| 6,190,548 B1 | 2/2001 | Frick |
| 6,197,081 B1 | 3/2001 | Schmidt |
| 6,200,469 B1 | 3/2001 | Wallace |
| 6,205,708 B1 | 3/2001 | Gatliff |
| 6,217,780 B1 | 4/2001 | Denkewicz, Jr. et al. |
| 6,242,230 B1 | 6/2001 | Batich et al. |
| 6,255,117 B1 | 7/2001 | Johnson |
| 6,264,841 B1 | 7/2001 | Tudor |
| 6,267,962 B1 | 7/2001 | Hart et al. |
| 6,271,020 B1 | 8/2001 | Coleman |
| 6,276,300 B1 | 8/2001 | Lewis, II et al. |
| 6,293,045 B1 | 9/2001 | Morgan |
| 6,319,405 B1 | 11/2001 | Roy et al. |
| 6,322,699 B1 | 11/2001 | Fernandez |
| 6,336,291 B1 | 1/2002 | Skuba |
| 6,337,025 B1 | 1/2002 | Clemenson |
| 6,337,203 B1 | 1/2002 | Beaulieu |
| 6,352,644 B1 | 3/2002 | Hawthorne et al. |
| 6,365,214 B1 | 4/2002 | Kirk |
| 6,365,384 B1 | 4/2002 | Iijima |
| 6,372,128 B1 | 4/2002 | Belhumeur |
| 6,378,244 B1 | 4/2002 | Iwata et al. |
| 6,403,366 B1 | 6/2002 | Kim |
| 6,406,627 B1 | 6/2002 | Wallace |
| 6,406,690 B1 | 6/2002 | Peleg et al. |
| 6,555,007 B1 | 4/2003 | Bilkey |
| 6,620,321 B2 | 9/2003 | Festa et al. |
| 6,638,959 B2 | 10/2003 | Howarth et al. |
| 6,749,748 B1 | 6/2004 | Macpherson et al. |
| 6,815,050 B2 | 11/2004 | Rainer |
| 6,890,651 B2 | 5/2005 | Bilkey |
| 7,341,671 B2 | 3/2008 | Shim et al. |
| 7,497,947 B2 | 3/2009 | Knighton et al. |
| 7,625,486 B2 | 12/2009 | Knighton et al. |
| 7,625,489 B2 | 12/2009 | Knighton et al. |
| 2001/0007065 A1 | 7/2001 | Blanchard et al. |
| 2001/0016721 A1 | 8/2001 | Salerno et al. |
| 2001/0025162 A1 | 9/2001 | Roe et al. |
| 2001/0027304 A1 | 10/2001 | Mayer |
| 2002/0134728 A1 | 9/2002 | Festa et al. |
| 2002/0139742 A1 | 10/2002 | Svirklys et al. |
| 2004/0031193 A1 | 2/2004 | Anderson |
| 2004/0112811 A1 | 6/2004 | Lindemulder |
| 2005/0036903 A1 | 2/2005 | Colclasure |
| 2006/0032123 A1 | 2/2006 | Knighton et al. |
| 2006/0032124 A1* | 2/2006 | Knighton ............... A01N 65/00 47/59 R |
| 2006/0231451 A1 | 10/2006 | Takeda et al. |
| 2008/0287367 A1 | 11/2008 | Hodges et al. |
| 2009/0120871 A1 | 5/2009 | Knighton et al. |
| 2009/0152185 A1 | 6/2009 | Knighton et al. |
| 2010/0320144 A1 | 12/2010 | Knighton et al. |
| 2011/0094949 A1 | 4/2011 | Just |
| 2011/0132835 A1 | 6/2011 | Knighton et al. |
| 2011/0163027 A1 | 7/2011 | Knighton et al. |
| 2011/0290720 A1 | 12/2011 | Knighton et al. |
| 2012/0125838 A1 | 5/2012 | Knighton et al. |
| 2012/0152828 A1 | 6/2012 | Fiegel et al. |
| 2013/0098841 A1 | 4/2013 | Fiegel et al. |

FOREIGN PATENT DOCUMENTS

| | | |
|---|---|---|
| CN | 1927393 A | 3/2007 |
| CN | 101720789 A | 6/2010 |
| DE | 103 52 460 A1 | 6/2005 |
| GB | 2 134 791 A | 8/1984 |
| GB | 2 134 793 A | 8/1984 |
| JP | 8-1188 A | 1/1996 |
| JP | 11-56096 A | 3/1999 |
| JP | 2001-62478 A | 3/2001 |
| JP | 2001-226991 A | 8/2001 |
| JP | 2002-360060 A | 12/2002 |
| JP | 2003112191 A | 4/2003 |
| KR | 20030053231 A | 6/2003 |
| SU | 810612 A1 | 3/1981 |
| WO | WO 97/07883 A1 | 3/1997 |
| WO | WO 2004/060049 A1 | 7/2004 |
| WO | WO 2005/081641 A2 | 9/2005 |

(56) References Cited

FOREIGN PATENT DOCUMENTS

| | | | |
|---|---|---|---|
| WO | WO 2005/102935 A2 | 11/2005 | |
| WO | WO 2006/109078 A1 | 10/2006 | |
| WO | WO 2007/077459 A2 | 7/2007 | |

OTHER PUBLICATIONS

Børsheim et al., "Preservation of Fish by Embedment in Sphagnum Moss, Peat or Holocellulose: Experimental Proof of the Oxopolysaccharidic Nature of the Preservative Substance and of its Antimicrobial and Tanning Action", ScienceDirect—Innovative Food Science & Emerging Technologies, vol. 2, Issue 1, Mar. 2001, pp. 63-74.

Diouf et al., Influence of Tropolone on Poria placenta Wood Degradation, AEM, 68(9):4377-4382 (Sep. 2002), HTTP://aem.asm.org/cgi/content/full/68/9/4377.

Gstoettner et al., "Accumulation of Cadmium, Chromium, and Zinc by the Moss Sphagnum Papillosum Lindle", Water, Air, and Soil Pollution, 93:321-330 (1997).

International Search Report for PCT Application No. PCT/US2005/012915, dated Jul. 26, 2005 (12 pages).

"Iron Chelator Prevents Bacterial Biofilm Formation", http://pubs.acs.org/cen, c & en, Jun. 3, 2002, p. 31.

Jones et al., "A Preliminary Study of Antimicrobial Activity in Some Malaysian Mosses (*Bryophytina*)", MALAYS. Appl. BIOL., 12(1):5-13 (1983).

Latiff et al., "The Effect of Moss Extracts on the Growth of Three Species of Bacteria", Malays. Appl. Biol., 18(1):77-84 (1989).

Martins et al., "Cadmium(II) and Zinc(II) Adsorption by the Aquatic Moss Fontinalis Antipyretica: Effect of Temperature pH and Water Hardness," Water Research, 38:693-699 (2004).

McCleary et al., "Mosses and Antibiosis", pp. 309-314 (date unknown).

Painter et al., "The Cation-Exchanger of Sphagnum Mosses: an Unusual Form of Holocellulose*", Carbohydrate Research, 66:C1-C3 (1978).

Podterob et al., "A History of the Medicinal Use of Plants of the Genus *Sphagnum*," Pharmaceutical Chemistry Journal, 36(4):192-194 (2002).

Smidsrød et al., "Contribution of Carbohydrates to the Catio-Exchange Selectivity of Aquatic Humus From Peat-Bog Water", Carbohydrate Research, 127:267-281 (1984).

Sphagnum papillosum-Lindberg[online]. Science Museum of Minnesota 2004-2005[retrieved on Dec. 2, 2009]. Retrieved from the Internet: <URL: http://www.sciencebuzz.org/museum/object/2000_12_sphagnum_papillosum_lindberg> (1 page).

Translation of the Jun. 6, 2008 First Office Action in Chinese Application No. 200580011538.1, filed Oct. 12, 2006 (7 pages).

Van Hoof et al., Antimicrobial and Antiviral Screening of Byryophyta, pp. 223-229 (date unknown).

Verhoeven et al., "The Ecological Significance of Organochemical Compounds in Sphagnum," Acta Rot. Neerl., 46(2):117-130 (Jun. 1997).

"Sphagnum cristatum" published in 2002 at http://www.anbg.gov.au/gnp/interns-2002/sphagnum-cristatum.html.

Jan. 25, 2012 Notification of Transmittal of the International Search Report and the Written Opinion of the International Searching Authority, or the Declaration for International Application No. PCT/US2011/049697 (10 pages).

Alavi et al., "Surface Sensing, Swarmer Cell Differentiation, and Biofilm Development," Methods in Enzymology, 336:29-40 (2001).

Battin et al., "Microbial Landscapes: New Paths to Biofilm Research," Nature Reviews, Microbiology, 5:76-81 (Jan. 2007).

Bott et al., "Biofilms in Flowing Systems," Methods in Enzymology, 337:88-103 (Feb. 2001).

Ceri et al., "The MBEC Assay System: Multiple Equivalent Biofilms for Antibiotic and Biocide Susceptibility Testing," Methods in Enzymology, 337:377-385 (2001).

Danese et al., "Biofilm Formation as a Developmental Process," Methods in Enzymology, 336:19-26 (2001).

Hall-Stoodley et al., "Bacterial Biofilms: From the Natural Environment to Infectious Diseases," Nature Reviews, Microbiology, 2:95-108 (Feb. 2004).

"A Guide to SpaNaturally and PoolNaturally", Creative Water Solutions LLC, 1864 Berkshire Lane North, Plymouth, MN 55441, Mar. 2009 (9 pages).

"Scientists Find Sphagnum Useful in Preserving Fish", Sichuan Animal & Veterinary Sciences, No. 9, 2001 (vol. 28, Sum 127, p. 56) (1 page).

Abstract for JP2003112191A (2 pages).

Nov. 6, 2015 Final Action in CA 2,779,715 (10 pages).

Sep. 9, 2014 Examiner's Report in CA 2,779,715 (3 pages).

May 7, 2014 Examiner's Report in CA 2,779,715 (3 pages).

Apr. 21, 2011 Opening your pool this summer the PoolNaturally way! [online], [retrieved on Feb. 11, 2014]. Retrieved from the Internet <URL:http://www.cwsnaturally.com/blog/uncategorized/opening-your-pool-this-summer-the-poolnaturally%c2%ae-way> (4 pages).

Jul. 20, 2009 Biofilm, Medical Devices, Your Pool or Spa [online], [retrieved on Feb. 11, 2014]. Retrieved from the Internet <URL:http://www.cwsnaturally.com/blog/biofilm/biofilm-medical-devices-your-pool-or-spa> (4 pages).

Jul. 19, 2013 First Examination Report in corresponding New Zealand Patent Application No. 606,972 (2 pages).

"Archive for the 'Biofilm' Category" webpage retrieved from http://www.cwsnaturally.com/blog/category/biofilm/ on Oct. 21, 2013, including Oct. 26, 2009 and Sep. 23, 2009 posts on pp. 9 to 13 of webpage (17 pages).

"Biofilm, Water and Sphagnum Moss" pdf retrieved from http://www.cwsnaturally.com/pdfs/Biofilm.pdf on Oct. 21, 2013, the New Zealand Examiner assigned a publication date of Aug. 18, 2009 (2 pages).

Parrs, "Removing Biofilms From Swimming Pools" webpage retrieved from http://ezinearticles.com/?id=2104823&Removing-Biofilms-From-Swimming-Pools= on Oct. 21, 2013, the New Zealand Examiner assigned a publication date of Mar. 15, 2009 (2 pages).

"Treating & Removing Biofilms in Spas & Hot tubs . . . " webpage retrieved from http://www.spacareonline.com/page/exotic/biofilm-removal.htm on Oct. 21, 2013, the New Zealand Examiner assigned a publication date of Sep. 8, 2009 (2 pages).

Knighton et al. "Community Service—While bacteria are easily treated with traditional sanitizers, biofilm requires a different approach" webpage retrieved from http://www.poolspanews.com/community-service/community-service.aspx an Oct. 21, 2013, posted Feb. 1, 2009 (4 pages).

Abstract for CN 101720789 A (1 page).

Abstract for CN 1316259 A (1 page).

Abstract for CN 1927393 A (1 page).

Mar. 3, 2014 Notice on the First Office Action for Chinese Application No. 201180041703.3 (7 pages).

Jul. 9, 2015 Supplementary Protest (3rd Protest) in Canadian Application No. 2,779,715 (9 pages).

Knighton and Fiegel, "Sphagnum Moss, Bacterial Biofilm, and Water Quality", Water Conditioning and Purification, Nov. 2008 (4 pages).

Knighton and Fiegel, "Technically Speaking, Community Service, While bacteria are easily treated with traditional sanitizers, biofilm requires a different approach", Pool and Spa News, Feb. 1, 2009 (2 pages).

Todd Woody, "Clean Pools, Less Chlorine . . . With Moss?", The New York Times, Aug. 28, 2009, 3 pages.

Ariel Schwartz, "Creative Water Solutions: Cleaning Your Pool Naturally, With Moss", Aug. 28, 2009, 3 pages, retrieved from www.fastcompany.com/1341619/creative-water-solutions-cleaning-your-pool-naturally-moss.

Rob Coz, "Using Sphagnum Moss as a Pool Purifier", Apr. 24, 2010, 3 pages, retrieved from www.blog.poolcenter.com/article.aspx?articleid=6105.

Machine Translation of DE 103 52 460 A1 (2005) (9 pages).

New World Encyclopedia. Sphagnum [online], [retrieved on Mar. 11, 2011]. Retrieved from the Internet <URL:http://www.newworldencyclopedia.org/entry/Sphagnum>.

(56) References Cited

OTHER PUBLICATIONS

English Language Translation of SU 810612 A2 (Lebedev et al.) completed by the USPTO on Aug. 2014, No. PTO 14/5493 (9 pages).
Abstract for DE 103 52 460 A1 (2005) (2 pages).
Complete Media Kit from the Apr. 21, 2009 version of the www.cwsnaturally.com website as archived by the Wayback Machine Internet Archive (http://web.archive.org/web/20101005102808/http://cwsnaturally.com/pdfs/CWSPPoolAndSpaNaturallyMediaKit2009.pdf) (13 pages).
May 1, 2014 Supplementary Protest (2nd Protest) in Canadian Application No. 2,779,715 (10 pages).

* cited by examiner

USE OF MOSS TO IMPROVE DENTAL HEALTH

FIELD OF THE INVENTION

This invention relates to methods of improving dental health using moss.

BACKGROUND OF THE INVENTION

Previous studies have demonstrated that sphagnum moss significantly inhibits the growth of free-floating (planktonic) bacteria. See U.S. Pat. No. 7,497,947 B2 and U.S. Patent Application Publication No. 2006/0032124 A1, both of which are incorporated by reference herein. Other studies have demonstrated that sphagnum moss inhibits and removes biofilm. See U.S. Patent Application Publication No. 2012/0152828 A1, which is incorporated by reference herein. "Sphagnum moss" is a generic expression that designates a range of botanical species that co-exist in a sphagnous bog. It should be noted that "peat moss" refers generally to a decomposed or composted sphagnum moss. Sphagnum moss is commonly harvested for use in various products. The petals, and not the stems, of the moss preferably may be harvested. Typically large pieces of plant material (roots, twigs, etc.) are removed. Excess water is removed and the moss is air dried. The moss may be compressed prior to packaging or shipment. Various additives may be used to alter the absorption characteristics or mechanical properties of the moss. Because sphagnum moss is readily available and relatively inexpensive, it has been used in a variety of products, primarily for the absorption of fluids.

There is need in the art for methods and products for improving dental health and methods and products for improving dental health using moss are described below.

SUMMARY OF THE INVENTION

The invention provides a method of improving dental health in a mammal comprising the mammal drinking at least 0.5 liters of water per day for a majority of the days of a period of at least one month, the water having been contacted with an amount of a non-decomposed moss effective to improve dental health as evidenced by a reduction in the pocket depths of the teeth of the mammal.

The invention provides a method of improving dental health in a mammal comprising the mammal's teeth being brushed using a toothpaste for a majority of the days of a period of at least one month, the toothpaste comprising an amount of a non-decomposed moss or non-decomposed moss extract effective to improve dental health as evidenced by a reduction in the pocket depths of the teeth.

The invention provides a toothpaste comprising an amount of a non-decomposed moss or non-decomposed moss extract effective to improve dental health as evidenced by a reduction in the pocket depths of the teeth of a mammal after the mammal's teeth have been brushed using the toothpaste for a majority of the days of a period of at least one month.

The invention provides a method of improving dental health in a mammal comprising the mammal's teeth being rinsed with a mouthwash for a majority of the days of a period of at least one month, the mouthwash containing an amount of a non-decomposed moss or non-decomposed moss extract effective to improve dental health as evidenced by a reduction in the pocket depths of the teeth.

The invention provides a mouthwash comprising an amount of a non-decomposed moss or non-decomposed moss extract effective to improve dental health as evidenced by a reduction in the pocket depths of the teeth of a mammal after the mammal's teeth have been rinsed with the mouthwash for a majority of the days of a period of at least one month.

The invention provides a toothpaste comprising a non-decomposed moss, wherein the concentration of non-decomposed moss ranges from 0.1 to 50 weight percent. The invention provides a toothpaste comprising a non-decomposed moss extract, wherein the concentration of non-decomposed moss extract ranges from 0.1 to 10 weight percent.

The invention provides a mouthwash comprising a non-decomposed moss, wherein the concentration of non-decomposed moss ranges from 0.01 to 5 weight percent. The invention provides a mouthwash comprising a non-decomposed moss extract, wherein the concentration of non-decomposed moss extract ranges from 0.01 to 95 weight percent.

It is to be understood that both the foregoing general description and the following detailed description are exemplary and explanatory and are intended to provide further explanation of the invention as claimed.

DETAILED DESCRIPTION OF THE PREFERRED EMBODIMENTS

The invention provides a method of improving dental health in a mammal comprising the mammal drinking at least 0.5 liters of water per day for a majority of the days of a period of at least one month, the water having been contacted with an amount of a non-decomposed moss effective to improve dental health as evidenced by a reduction in the pocket depths of the teeth of the mammal. In an embodiment, the mammal drinks at least one liter of the contacted water per day. In one embodiment, the mammal drinks at least 0.5 liters of the contacted water per day for a majority of the days of a period of at least three months. In an embodiment, the mammal drinks at least 0.5 liters of the contacted water per day for a majority of the days of a period of at least six months. In one embodiment, the mammal is a human.

In an embodiment, the non-decomposed moss is selected from the group consisting of sphagnum papillosum, sphagnum cristatum, and mixtures thereof. In one embodiment, the non-decomposed moss is in the form of leaves or parts of leaves. In an embodiment, the non-decomposed moss is in the form of compressed leaves or parts of leaves. In one embodiment, the non-decomposed moss is placed in a carrier. In an embodiment, the carrier is a mesh bag. In one embodiment, the water is contacted with the mesh bag containing the non-decomposed moss in a drinking water bottle. A drinking water bottle is a bottle that consumers refill and carry with them to consume water during the day. Such a water bottle typically has a capacity of from 12 to 64 ounces.

In one embodiment, at least 20 percent of the pocket depths that had higher than a 3 mm value before the mammal started drinking the contacted water are reduced by 20 percent or more after one month of drinking at least 0.5 liters of the contacted water per day for a majority of the days of the month. In an embodiment, at least 20 percent of the pocket depths that had higher than a 3 mm value before the mammal started drinking the contacted water are reduced by 40 percent or more after one month of drinking at least 0.5 liters of the contacted water per day for a majority of the days of the month. In one embodiment, at least 40 percent of the pocket depths that had higher than a 3 mm value before the mammal started drinking the contacted water are reduced by 40 percent or more after one month of drinking at least 0.5 liters of the contacted water per day for a majority of the days of the month.

In an embodiment, at least 20 percent of the pocket depths that had higher than a 3 mm value before the mammal started drinking the contacted water are reduced by 20 percent or more after three months of drinking at least 0.5 liters of the contacted water per day for a majority of the days of the three months. In one embodiment, at least 20 percent of the pocket depths that had higher than a 3 mm value before the mammal started drinking the contacted water are reduced by 40 percent or more after three months of drinking at least 0.5 liters of the contacted water per day for a majority of the days of the three months. In an embodiment, at least 40 percent of the pocket depths that had higher than a 3 mm value before the mammal started drinking the contacted water are reduced by 40 percent or more after three months of drinking at least 0.5 liters of the contacted water per day for a majority of the days of the three months.

In one embodiment, at least 20 percent of the pocket depths that had higher than a 3 mm value before the mammal started drinking the contacted water are reduced by 20 percent or more after six months of drinking at least 0.5 liters of the contacted water per day for a majority of the days of the six months. In an embodiment, at least 20 percent of the pocket depths that had higher than a 3 mm value before the mammal started drinking the contacted water are reduced by 40 percent or more after six months of drinking at least 0.5 liters of the contacted water per day for a majority of the days of the six months. In one embodiment, at least 40 percent of the pocket depths that had higher than a 3 mm value before the mammal started drinking the contacted water are reduced by 40 percent or more after six months of drinking at least 0.5 liters of the contacted water per day for a majority of the days of the six months.

The invention provides a method of improving dental health in a mammal comprising the mammal's teeth being brushed using a toothpaste for a majority of the days of a period of at least one month, the toothpaste comprising an amount of a non-decomposed moss or non-decomposed moss extract effective to improve dental health as evidenced by a reduction in the pocket depths of the teeth. In an embodiment, at least 20 percent of the pocket depths that had higher than a 3 mm value before the mammal started brushing with the toothpaste are reduced by 20 percent or more after one month of brushing with the toothpaste for a majority of the days of the month. In one embodiment, at least 20 percent of the pocket depths that had higher than a 3 mm value before the mammal started brushing with the toothpaste are reduced by 40 percent or more after one month of brushing with the toothpaste for a majority of the days of the month. In an embodiment, at least 40 percent of the pocket depths that had higher than a 3 mm value before the mammal started brushing with the toothpaste are reduced by 40 percent or more after one month of brushing with the toothpaste for a majority of the days of the month.

In one embodiment, at least 20 percent of the pocket depths that had higher than a 3 mm value before the mammal started brushing with the toothpaste are reduced by 20 percent or more after three months of brushing with the toothpaste for a majority of the days of the three months. In an embodiment, at least 20 percent of the pocket depths that had higher than a 3 mm value before the mammal started brushing with the toothpaste are reduced by 40 percent or more after three months of brushing with the toothpaste for a majority of the days of the three months. In one embodiment, at least 40 percent of the pocket depths that had higher than a 3 mm value before the mammal started brushing with the toothpaste are reduced by 40 percent or more after three months of brushing with the toothpaste for a majority of the days of the three months.

In an embodiment, at least 20 percent of the pocket depths that had higher than a 3 mm value before the mammal started brushing with the toothpaste are reduced by 20 percent or more after six months of brushing with the toothpaste for a majority of the days of the six months. In one embodiment, at least 20 percent of the pocket depths that had higher than a 3 mm value before the mammal started brushing with the toothpaste are reduced by 40 percent or more after six months of brushing with the toothpaste for a majority of the days of the six months. In an embodiment, at least 40 percent of the pocket depths that had higher than a 3 mm value before the mammal started brushing with the toothpaste are reduced by 40 percent or more after six months of brushing with the toothpaste for a majority of the days of the six months. In one embodiment, the mammal is a human. In one embodiment, the toothpaste comprises a non-decomposed moss. In an embodiment, the toothpaste comprises a non-decomposed moss extract. In an embodiment, the non-decomposed moss is selected from the group consisting of sphagnum papillosum, sphagnum cristatum, and mixtures thereof. In one embodiment, the non-decomposed moss extract is selected from the group consisting of an extract of sphagnum papillosum, an extract of sphagnum cristatum, and mixtures thereof. In an embodiment, the concentration of non-decomposed moss ranges from 0.1 to 50 weight percent. In one embodiment, the concentration of non-decomposed moss extract ranges from 0.1 to 10 weight percent.

The invention provides a toothpaste comprising an amount of a non-decomposed moss or non-decomposed moss extract effective to improve dental health as evidenced by a reduction in the pocket depths of the teeth of a mammal after the mammal's teeth have been brushed using the toothpaste for a majority of the days of a period of at least one month. In an embodiment, at least 20 percent of the pocket depths that had higher than a 3 mm value before the mammal started brushing with the toothpaste are reduced by 20 percent or more after one month of brushing with the toothpaste for a majority of the days of the month. In one embodiment, at least 20 percent of the pocket depths that had higher than a 3 mm value before the mammal started brushing with the toothpaste are reduced by 40 percent or more after one month of brushing with the toothpaste for a majority of the days of the month. In an embodiment, at least 40 percent of the pocket depths that had higher than a 3 mm value before the mammal started brushing with the toothpaste are reduced by 40 percent or more after one month of brushing with the toothpaste for a majority of the days of the month.

In one embodiment, at least 20 percent of the pocket depths that had higher than a 3 mm value before the mammal started brushing with the toothpaste are reduced by 20 percent or more after three months of brushing with the toothpaste for a majority of the days of the three months. In an embodiment, at least 20 percent of the pocket depths that had higher than a 3 mm value before the mammal started brushing with the toothpaste are reduced by 40 percent or more after three months of brushing with the toothpaste for a majority of the days of the three months. In one embodiment, at least 40 percent of the pocket depths that had higher than a 3 mm value before the mammal started brushing with the toothpaste are reduced by 40 percent or more after three months of brushing with the toothpaste for a majority of the days of the three months.

In an embodiment, at least 20 percent of the pocket depths that had higher than a 3 mm value before the mammal started brushing with the toothpaste are reduced by 20 percent or more after six months of brushing with the toothpaste for a majority of the days of the six months. In one embodiment, at least 20 percent of the pocket depths that had higher than a 3 mm value before the mammal started brushing with the toothpaste are reduced by 40 percent or more after six months of brushing with the toothpaste for a majority of the days of the six months. In an embodiment, at least 40 percent of the pocket depths that had higher than a 3 mm value before the mammal started brushing with the toothpaste are reduced by 40 percent or more after six months of brushing with the toothpaste for a majority of the days of the six months. In one embodiment, the mammal is a human. In an embodiment, the toothpaste comprises a non-decomposed moss. In one embodiment, the toothpaste comprises a non-decomposed moss extract. In an embodiment, the non-decomposed moss is selected from the group consisting of sphagnum papillosum, sphagnum cristatum, and mixtures thereof. In one embodiment, the non-decomposed moss extract is selected from the group consisting of an extract of sphagnum papillosum, an extract of sphagnum cristatum, and mixtures thereof. In an embodiment, the concentration of non-decomposed moss ranges from 0.1 to 50 weight percent. In one embodiment, the concentration of non-decomposed moss extract ranges from 0.1 to 10 weight percent.

The invention provides a method of improving dental health in a mammal comprising the mammal's teeth being rinsed with a mouthwash for a majority of the days of a period of at least one month, the mouthwash containing an amount of a non-decomposed moss or non-decomposed moss extract effective to improve dental health as evidenced by a reduction in the pocket depths of the teeth. In an embodiment, at least 20 percent of the pocket depths that had higher than a 3 mm value before the mammal started rinsing with the mouthwash are reduced by 20 percent or more after one month of rinsing with the mouthwash for a majority of the days of the month. In one embodiment, at least 20 percent of the pocket depths that had higher than a 3 mm value before the mammal started rinsing with the mouthwash are reduced by 40 percent or more after one month of rinsing with the mouthwash for a majority of the days of the month. In an embodiment, at least 40 percent of the pocket depths that had higher than a 3 mm value before the mammal started rinsing with the mouthwash are reduced by 40 percent or more after one month of rinsing with the mouthwash for a majority of the days of the month.

In one embodiment, at least 20 percent of the pocket depths that had higher than a 3 mm value before the mammal started rinsing with the mouthwash are reduced by 20 percent or more after three months of rinsing with the mouthwash for a majority of the days of the three months. In an embodiment, at least 20 percent of the pocket depths that had higher than a 3 mm value before the mammal started rinsing with the mouthwash are reduced by 40 percent or more after three months of rinsing with the mouthwash for a majority of the days of the three months. In one embodiment, at least 40 percent of the pocket depths that had higher than a 3 mm value before the mammal started rinsing with the mouthwash are reduced by 40 percent or more after three months of rinsing with the mouthwash for a majority of the days of the three months.

In an embodiment, at least 20 percent of the pocket depths that had higher than a 3 mm value before the mammal started rinsing with the mouthwash are reduced by 20 percent or more after six months of rinsing with the mouthwash for a majority of the days of the six months. In one embodiment, at least 20 percent of the pocket depths that had higher than a 3 mm value before the mammal started rinsing with the mouthwash are reduced by 40 percent or more after six months of rinsing with the mouthwash for a majority of the days of the six months. In an embodiment, at least 40 percent of the pocket depths that had higher than a 3 mm value before the mammal started rinsing with the mouthwash are reduced by 40 percent or more after six months of rinsing with the mouthwash for a majority of the days of the six months. In one embodiment, the mammal is a human. In an embodiment, the mouthwash comprises a non-decomposed moss. In one embodiment, the mouthwash comprises a non-decomposed moss extract. In an embodiment, the non-decomposed moss is selected from the group consisting of sphagnum papillosum, sphagnum cristatum, and mixtures thereof. In one embodiment, the non-decomposed moss extract is selected from the group consisting of an extract of sphagnum papillosum, an extract of sphagnum cristatum, and mixtures thereof. In an embodiment, the concentration of non-decomposed moss ranges from 0.01 to 5 weight percent. In one embodiment, the concentration of non-decomposed moss extract ranges from 0.01 to 95 weight percent.

The invention provides a mouthwash comprising an amount of a non-decomposed moss or non-decomposed moss extract effective to improve dental health as evidenced by a reduction in the pocket depths of the teeth of a mammal after the mammal's teeth have been rinsed with the mouthwash for a majority of the days of a period of at least one month. In an embodiment, at least 20 percent of the pocket depths that had higher than a 3 mm value before the mammal started rinsing with the mouthwash are reduced by 20 percent or more after one month of rinsing with the mouthwash for a majority of the days of the month. In one embodiment, at least 20 percent of the pocket depths that had higher than a 3 mm value before the mammal started rinsing with the mouthwash are reduced by 40 percent or more after one month of rinsing with the mouthwash for a majority of the days of the month. In an embodiment, at least 40 percent of the pocket depths that had higher than a 3 mm value before the mammal started rinsing with the mouthwash are reduced by 40 percent or more after one month of rinsing with the mouthwash for a majority of the days of the month.

In one embodiment, at least 20 percent of the pocket depths that had higher than a 3 mm value before the mammal started rinsing with the mouthwash are reduced by 20 percent or more after three months of rinsing with the mouthwash for a majority of the days of the three months. In an embodiment, at least 20 percent of the pocket depths that had higher than a 3 mm value before the mammal started rinsing with the mouthwash are reduced by 40 percent or more after three months of rinsing with the mouthwash for a majority of the days of the three months. In one embodiment, at least 40 percent of the pocket depths that had higher than a 3 mm value before the mammal started rinsing with the mouthwash are reduced by 40 percent or more after three months of rinsing with the mouthwash for a majority of the days of the three months.

In an embodiment, at least 20 percent of the pocket depths that had higher than a 3 mm value before the mammal started rinsing with the mouthwash are reduced by 20 percent or more after six months of rinsing with the mouthwash for a majority of the days of the six months. In one embodiment, at least 20 percent of the pocket depths that had higher than a 3 mm value before the mammal started rinsing with the mouthwash are reduced by 40 percent or more after six months of rinsing with the mouthwash for a majority of the days of the six months. In an embodiment, at least 40 percent of the pocket depths that had higher than a 3 mm value before the mammal started rinsing with the mouthwash are reduced by 40 percent or more after six months of rinsing with the mouthwash for a majority of the days of the six months. In one embodiment, the mammal is a human. In an embodiment, the mouthwash comprises a non-decomposed moss. In one embodiment, the mouthwash comprises a non-decomposed moss extract. In an embodiment, the non-decomposed moss is selected from the group consisting of sphagnum papillosum, sphagnum cristatum, and mixtures thereof. In one embodiment, the non-decomposed moss extract is selected from the group consisting of an extract of sphagnum papillosum, an extract of sphagnum cristatum, and mixtures thereof. In an embodiment, the concentration of non-decomposed moss ranges from 0.01 to 5 weight percent. In one embodiment, the concentration of non-decomposed moss extract ranges from 0.01 to 95 weight percent.

The invention provides a toothpaste comprising a non-decomposed moss, wherein the concentration of non-decomposed moss ranges from 0.1 to 50 weight percent. In one embodiment, the non-decomposed moss is selected from the group consisting of sphagnum papillosum, sphagnum cristatum, and mixtures thereof.

The invention provides a toothpaste comprising a non-decomposed moss extract, wherein the concentration of non-decomposed moss extract ranges from 0.1 to 10 weight percent. In one embodiment, the non-decomposed moss extract is selected from the group consisting of an extract of sphagnum papillosum, an extract of sphagnum cristatum, and mixtures thereof.

The invention provides a mouthwash comprising a non-decomposed moss, wherein the concentration of non-decomposed moss ranges from 0.01 to 5 weight percent. In one embodiment, the non-decomposed moss is selected from the group consisting of sphagnum papillosum, sphagnum cristatum, and mixtures thereof.

The invention provides a mouthwash comprising a non-decomposed moss extract, wherein the concentration of non-decomposed moss extract ranges from 0.01 to 95 weight percent. In one embodiment, the non-decomposed moss extract is selected from the group consisting of an extract of sphagnum papillosum, an extract of sphagnum cristatum, and mixtures thereof.

The various parameters such as moss used or amount the pocket depths are reduced can apply to drinking the moss treated water, brushing teeth, a toothpaste, using a mouthwash, or a mouthwash.

In certain embodiments, the moss is enclosed or encapsulated in a mesh material that prevents the moss from disintegrating in an aqueous environment. Preferred mesh materials include those comprising polymers such as nylon or polypropylene, with mesh sizes ranging from about 0.1 to 1 mm. Polymers are generally preferred because they are inexpensive and may be resistant to degradation.

Suitable for use in this invention are *S. papillosum*, which can be harvested from bogs in northern Minnesota, U.S.A., and *S. cristatum*, which is commercially available as a compressed board from Coastpak Holdings, Ltd., Hokitika, New Zealand. These species of moss can be used by themselves or together in the devices and systems of this invention. Typically and preferably the moss is cleaned to remove small particles, such as dirt, and larger debris, such as roots and leaves. Commercially available moss may be fumigated before it is packaged by a manufacturer in order to destroy seeds.

In a preferred embodiment, the moss is cut by mechanical means into a desired size and shape. The moss preferably is then sterilized by autoclaving, exposure to ethylene oxide, or by other means known to one of skill in the art. Sterilization destroys living organisms in the moss and thus avoids any problems of undesirable or foreign bacteria being introduced into the environment where a device of this invention is used. The moss is then ready for use. A carrier can be a polymer matrix, a biomatrix, membrane, gel, hydrogel, or mesh bag.

The moss can be compressed and can be in the form of strips or bricks. The moss can be sterilized by autoclaving, sterilized by chemical treatment, or sterilized by treatment with ethylene oxide. The moss can be washed with an acidic solution, especially a solution of acetic acid. The moss can be washed with an acidic solution and then washed with a salt solution.

The moss can be prepared by (i) drying non-decomposed moss; and (ii) sterilizing the moss. The method can further comprising compressing the moss, compressing the moss and cutting the moss into strips, sterilizing the moss by autoclaving, chemical treatment, or treatment with ethylene oxide.

The moss can be prepared by (i) contacting non-decomposed moss with an acidic solution; and (ii) drying the moss. The method can comprise contacting the non-decomposed moss with a salt solution after step (i). In one embodiment, the acidic solution is a solution of acetic acid.

In certain embodiments a non-decomposed moss extract is used. The extract can be prepared by contacting the moss with water or another appropriate solvent such as an alcohol and then straining or otherwise separating the largest components of the moss from the water or other solvent. In certain embodiments a toothpaste or mouthwash is provided or used. Both toothpastes and mouthwashes and their common components are very well known in the art. Known carriers, solvents, thickeners, emulsifiers, etc. can be used. For instance, a mouthwash may contain water, alcohol, flavoring, coloring, and non-decomposed moss or a non-decomposed moss extract. A toothpaste may contain an abrasive, fluoride, surfactant, flavoring, coloring, and non-decomposed moss or a non-decomposed moss extract.

EXAMPLE

A sixty-two year old man's teeth were evaluated at the dentist using the periodontal probe test for the depth of tooth pockets. In this standard test a periodontal probe is used to place a light pressure of 10 to 20 grams into the gingival sulcus, which is an area of potential space between a tooth and the surrounding tissue. The periodontal probe has a bent or curved end portion. The main body of the periodontal probe is advanced parallel to the contours of the root of the tooth to insert the probe down to the base of the pocket. This movement results in a section of the end portion of the periodontal probe being obscured by the surrounding tissue. The first marking visible above the pocket indicates the measurement of the pocket depth. A healthy pocket depth is about 3 mm. Depths greater than 3 mm can be associated with attachment loss of the tooth to the surrounding alveolar bone or gingival hyperplasia. A first evaluation was performed (results shown in Table 1 below) and a second evaluation (results shown in Table 2 below) was performed approximately a year later by the same dentist. All evaluations in this example were performed by the same dentist.

Approximately six months after the second evaluation, the man began drinking moss treated water. The man placed a small nylon mesh bag containing 0.4 g of compacted sphagnum moss (Sphagnum cristatum) into a 24 ounce (0.71 L) water bottle and periodically refilled this water bottle two to three times a day and consumed the moss treated water. The sphagnum moss was obtained from Coastpak Holdings, Ltd., Hokitika, New Zealand. The man drank this water nearly every day for six months until his third evaluation was performed. The moss in the water bottle was changed once a month. The results of this third evaluation are shown in Table 3 below. A dash in the tables below indicates a pocket depth value of 3 mm or less (normal/healthy); the values of "4" and "5" and "6" are in millimeters. Each tooth is measured on the facial (front) and lingual (back) sides of the tooth. Three pocket depth measurements (side, center, and side) are made on each of the facial and lingual sides.

The man continued to drink the moss treated water nearly every day as described above and fourth, fifth, sixth, and seventh evaluations were performed at intervals of approximately five months and these results are shown in Tables 4 to 7 below.

TABLE 1

| Tooth | 1 | 2 | 3 | 4 | 5 | 6 | 7 | 8 |
|---|---|---|---|---|---|---|---|---|
| Facial | X | - - - | - - 4 | - - 4 | 4 - 5 | 4 - - | - - 4 | - - 4 |
| Lingual | X | 4 - 4 | 4 - 5 | - - 4 | - - 4 | - - 4 | 4 - 4 | - - 4 |

| Tooth | 9 | 10 | 11 | 12 | 13 | 14 | 15 | 16 |
|---|---|---|---|---|---|---|---|---|
| Facial | 4 - - | - - 4 | 4 - 4 | 4 - - | 4 4 - | - - 4 | 4 - - | X |
| Lingual | 4 - 4 | - - - | - - - | 4 - - | 4 - - | - - - | 4 - 4 | X |

| Tooth | 17 | 18 | 19 | 20 | 21 | 22 | 23 | 24 |
|---|---|---|---|---|---|---|---|---|
| Facial | X | 4 - - | 4 - 4 | - - - | - - - | 4 - - | - - - | 4 - - |
| Lingual | X | 4 - - | 4 - 4 | - - 4 | - - - | - - - | - - - | - - - |

| Tooth | 25 | 26 | 27 | 28 | 29 | 30 | 31 | 32 |
|---|---|---|---|---|---|---|---|---|
| Facial | - - 4 | - - 4 | - - 4 | - - 4 | - - 4 | - - - | 4 - 4 | X |
| Lingual | - - - | - - - | - - 4 | - - 4 | - - - | 4 - 4 | 4 - 4 | X |

TABLE 2

| Tooth | 1 | 2 | 3 | 4 | 5 | 6 | 7 | 8 |
|---|---|---|---|---|---|---|---|---|
| Facial | X | - - - | - - 4 | 4 - 4 | - - 4 | - - 4 | 4 - 4 | 4 - - |
| Lingual | X | - - 4 | 4 - 5 | - - 4 | 4 - 4 | - - 5 | 4 - 4 | 4 - 5 |

| Tooth | 9 | 10 | 11 | 12 | 13 | 14 | 15 | 16 |
|---|---|---|---|---|---|---|---|---|
| Facial | 5 - 4 | 4 - - | 4 - - | 5 - 4 | 4 - 4 | - - - | - - 4 | X |
| Lingual | 5 - - | 4 - 4 | 4 - - | 4 - - | - - - | 4 - - | 4 - 4 | X |

| Tooth | 17 | 18 | 19 | 20 | 21 | 22 | 23 | 24 |
|---|---|---|---|---|---|---|---|---|
| Facial | X | 4 - 4 | - - 4 | 4 - - | - - - | 4 - - | - - 4 | - - 4 |
| Lingual | X | 4 - 4 | 4 - 4 | - - 4 | - - 4 | - - - | - - - | - - - |

| Tooth | 25 | 26 | 27 | 28 | 29 | 30 | 31 | 32 |
|---|---|---|---|---|---|---|---|---|
| Facial | 4 - 4 | 4 - 4 | - - 4 | 4 - - | - - 4 | 4 - 4 | - - - | X |
| Lingual | - - - | 4 - - | 4 - 4 | - - - | 4 - - | 4 - 4 | 4 - 4 | X |

TABLE 3

| Tooth | 1 | 2 | 3 | 4 | 5 | 6 | 7 | 8 |
|---|---|---|---|---|---|---|---|---|
| Facial | X | - - - | - - - | - - - | - - 4 | - - - | - - - | - - - |
| Lingual | X | - - 4 | 4 - 5 | 4 - 4 | 4 - 4 | - - - | 4 - - | - - 4 |

| Tooth | 9 | 10 | 11 | 12 | 13 | 14 | 15 | 16 |
|---|---|---|---|---|---|---|---|---|
| Facial | 4 - - | 4 - - | 4 - 4 | - - - | 4 - - | - - - | 4 - - | X |
| Lingual | 4 - - | - - - | - - - | - - - | - - - | - - - | - - - | X |

| Tooth | 17 | 18 | 19 | 20 | 21 | 22 | 23 | 24 |
|---|---|---|---|---|---|---|---|---|
| Facial | X | - - - | 4 - - | - - - | - - - | - - - | - - - | - - - |
| Lingual | X | - - 4 | - - - | - - - | - - - | - - - | - - - | - - - |

| Tooth | 25 | 26 | 27 | 28 | 29 | 30 | 31 | 32 |
|---|---|---|---|---|---|---|---|---|
| Facial | - - - | - - - | - - - | - - - | - - - | - - 4 | - - - | X |
| Lingual | - - - | - - - | - - - | - - - | - - - | 4 - 4 | - - 4 | X |

TABLE 4

| Tooth | 1 | 2 | 3 | 4 | 5 | 6 | 7 | 8 |
|---|---|---|---|---|---|---|---|---|
| Facial | X | - - - | - - - | - - 4 | - - - | - - - | - - - | - - - |
| Lingual | X | - - 4 | - - 4 | - - 4 | - - - | - - - | - - - | - - 4 |

| Tooth | 9 | 10 | 11 | 12 | 13 | 14 | 15 | 16 |
|---|---|---|---|---|---|---|---|---|
| Facial | 4 - - | - - - | - - - | 4 - 4 | 4 - - | - - - | - - - | X |
| Lingual | - - - | - - - | - - - | - - - | - - - | - - - | - - 4 | X |

| Tooth | 17 | 18 | 19 | 20 | 21 | 22 | 23 | 24 |
|---|---|---|---|---|---|---|---|---|
| Facial | X | - - - | - - - | - - - | - - - | 4 - - | - - 4 | - - - |
| Lingual | X | 4 4 4 | - - - | - - - | - - - | - - - | - - - | - - - |

| Tooth | 25 | 26 | 27 | 28 | 29 | 30 | 31 | 32 |
|---|---|---|---|---|---|---|---|---|
| Facial | - - - | - - - | - - 4 | - - - | - - - | - - - | - - - | X |
| Lingual | - - - | - - - | - - - | - - - | - - - | - - 4 | - - 4 | X |

TABLE 5

| Tooth | 1 | 2 | 3 | 4 | 5 | 6 | 7 | 8 |
|---|---|---|---|---|---|---|---|---|
| Facial | X | - - - | 4 - - | - - - | - - - | - - - | - - - | - - - |
| Lingual | X | 5 - 5 | 4 - 6 | - - - | - - - | - - - | - - - | - - 5 |

| Tooth | 9 | 10 | 11 | 12 | 13 | 14 | 15 | 16 |
|---|---|---|---|---|---|---|---|---|

TABLE 5-continued

| Facial | 4 - - | 4 - - | 4 - 4 | 4 - - | - - - | - - - | 4 - - | X |
| Lingual | 4 - - | - - - | - - - | - - - | - - - | - - - | 4 - - | X |

| Tooth | 17 | 18 | 19 | 20 | 21 | 22 | 23 | 24 |
|---|---|---|---|---|---|---|---|---|
| Facial | X | 4 - - | - - 4 | - - - | - - - | - - - | - - - | - - - |
| Lingual | X | - 4 - | 4 4 4 | - - - | - - - | - - - | - - - | - - - |

| Tooth | 25 | 26 | 27 | 28 | 29 | 30 | 31 | 32 |
|---|---|---|---|---|---|---|---|---|
| Facial | - - - | - - - | - - 4 | - - - | - - - | - - - | - - - | X |
| Lingual | - - - | - - - | - - - | - - - | - - - | 4 - - | - - 4 | X |

TABLE 6

| Tooth | 1 | 2 | 3 | 4 | 5 | 6 | 7 | 8 |
|---|---|---|---|---|---|---|---|---|
| Facial | X | - - 4 | - - - | - - - | - - 4 | - - - | - - - | - - 4 |
| Lingual | X | 4 - 4 | 4 - 5 | - - 4 | - - 4 | - - - | - - - | - - - |

| Tooth | 9 | 10 | 11 | 12 | 13 | 14 | 15 | 16 |
|---|---|---|---|---|---|---|---|---|
| Facial | 4 - - | - - - | - - - | 4 - - | - - - | - - - | - - - | X |
| Lingual | - - - | - - - | - - - | - - - | - - - | - 4 4 | - - - | X |

| Tooth | 17 | 18 | 19 | 20 | 21 | 22 | 23 | 24 |
|---|---|---|---|---|---|---|---|---|
| Facial | X | - - - | - - - | - - - | - - - | - - - | - - - | - - - |
| Lingual | X | 4 - - | 4 - 4 | - - - | - - - | - - - | - - - | - - - |

| Tooth | 25 | 26 | 27 | 28 | 29 | 30 | 31 | 32 |
|---|---|---|---|---|---|---|---|---|
| Facial | - - - | - - - | - - - | - - - | - - - | - - - | - - 4 | X |
| Lingual | - - - | - - - | - - - | - - - | - - - | - 4 - | - - - | X |

TABLE 7

| Tooth | 1 | 2 | 3 | 4 | 5 | 6 | 7 | 8 |
|---|---|---|---|---|---|---|---|---|
| Facial | X | - - - | - - - | - - - | - - - | - - 4 | - - - | - - 4 |
| Lingual | X | 4 - 4 | 4 - 5 | - - 4 | - - 5 | - - 4 | - - - | - - 4 |

| Tooth | 9 | 10 | 11 | 12 | 13 | 14 | 15 | 16 |
|---|---|---|---|---|---|---|---|---|
| Facial | - - - | - - - | - - - | 4 - - | 4 - - | - - - | - - - | X |
| Lingual | 4 - - | - - - | - - - | - - - | - - - | - - - | 4 - - | X |

| Tooth | 17 | 18 | 19 | 20 | 21 | 22 | 23 | 24 |
|---|---|---|---|---|---|---|---|---|
| Facial | X | - - - | - - - | - - - | - - - | - - - | - - - | - - - |
| Lingual | X | 4 - 4 | - - - | - - - | - - - | - - - | - - - | - - - |

| Tooth | 25 | 26 | 27 | 28 | 29 | 30 | 31 | 32 |
|---|---|---|---|---|---|---|---|---|
| Facial | - - - | - - - | - - - | - - - | - - - | - - 4 | - - - | X |
| Lingual | - - - | - - - | - - - | - - - | - - - | 4 4 - | - - - | X |

As shown above, the pocket depths of many of the teeth were reduced or eliminated by drinking the moss treated water. Table 3 shows the first evaluation after the man began drinking moss treated water. As shown in Table 3, teeth 6, 12, 14, and 20 to 29 had no unhealthy pocket depths. In Tables 1 and 2, before the man began drinking moss treated water, teeth 6, 12, 14, and 20 to 29 did have measured pocket depths of "4" or "5" (unhealthy).

In addition, each table shows 84 measurements (three for each of 28 teeth). Before treatment with moss treated water, there were 54 measurements above "3" (Table 1) and 67 measurements above "3" (Table 2). After treatment with moss treated water, there were 23, 18, 23, 18, and 19 measurements above "3" (Tables 3 to 7, respectively).

The above description and the drawing are provided for the purpose of describing embodiments of the invention and are not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A method of improving the dental health of a mammal in need thereof comprising said mammal in need thereof drinking at least 0.5 liters of water per day for a majority of the days of a period of at least one month wherein said water contains a therapeutically effective amount of a non-decomposed moss selected from the group consisting of sphagnum *papillosum*, sphagnum *cristatum* and mixtures thereof to improve the dental health of the mammal in need thereof as evidenced by a reduction in the pocket depths of the teeth of the mammal.

2. The method of claim 1, wherein the mammal drinks at least one liter of the water per day.

3. The method of claim 1, wherein the mammal drinks at least 0.5 liters of the water per day for a majority of the days of a period of at least three months.

4. The method of claim 1, wherein the mammal drinks at least 0.5 liters of the water per day for a majority of the days of a period of at least six months.

5. The method of claim 1, wherein the mammal is a human.

6. The method of claim 1, wherein the non-decomposed moss is the leaves or parts of the leaves of the moss.

7. The method of claim 6, wherein the leaves or parts of the leaves of the moss are compressed leaves or compressed parts of leaves.

8. The method of claim 1, wherein the non-decomposed moss is placed in a carrier.

9. The method of claim 8, wherein the carrier is a mesh bag.

10. The method of claim 9, wherein the mesh bag is disposed in a drinking water bottle.

11. The method of claim 1, wherein at least 20 percent of the pocket depths that had higher than a 3 mm value before the mammal started drinking the water are reduced by 20 percent or more after one month of drinking at least 0.5 liters of the water per day for a majority of the days of the month.

12. The method of claim 1, wherein at least 20 percent of the pocket depths that had higher than a 3 mm value before the mammal started drinking the water are reduced by 40 percent or more after one month of drinking at least 0.5 liters of the water per day for a majority of the days of the month.

13. The method of claim 1, wherein at least 40 percent of the pocket depths that had higher than a 3 mm value before the mammal started drinking the water are reduced by 40 percent or more after one month of drinking at least 0.5 liters of the water per day for a majority of the days of the month.

14. The method of claim 1, wherein at least 20 percent of the pocket depths that had higher than a 3 mm value before the mammal started drinking the water are reduced by 20 percent or more after three months of drinking at least 0.5 liters of the water per day for a majority of the days of the three months.

15. The method of claim 1, wherein at least 20 percent of the pocket depths that had higher than a 3 mm value before the mammal started drinking the water are reduced by 40 percent or more after three months of drinking at least 0.5 liters of the water per day for a majority of the days of the three months.

16. The method of claim 1, wherein at least 40 percent of the pocket depths that had higher than a 3 mm value before the mammal started drinking the water are reduced by 40 percent or more after three months of drinking at least 0.5 liters of the water per day for a majority of the days of the three months.

17. The method of claim 1, wherein at least 20 percent of the pocket depths that had higher than a 3 mm value before the mammal started drinking the water are reduced by 20 percent or more after six months of drinking at least 0.5 liters of the water per day for a majority of the days of the six months.

18. The method of claim 1, wherein at least 20 percent of the pocket depths that had higher than a 3 mm value before the mammal started drinking the water are reduced by 40 percent or more after six months of drinking at least 0.5 liters of the water per day for a majority of the days of the six months.

19. The method of claim 1, wherein at least 40 percent of the pocket depths that had higher than a 3 mm value before the mammal started drinking the water are reduced by 40 percent or more after six months of drinking at least 0.5 liters of the water per day for a majority of the days of the six months.

* * * * *